United States Patent
Chung

(10) Patent No.: US 7,603,797 B2
(45) Date of Patent: Oct. 20, 2009

(54) PORTABLE SHOE

(76) Inventor: Chu-Yun Chung, 5F, No. 9-1, Ln. 15, Ko Chiang Rd., Shihlin Dist., Taipei City (TW)

( * ) Notice: Subject to any disclaimer, the term of this patent is extended or adjusted under 35 U.S.C. 154(b) by 544 days.

(21) Appl. No.: 11/549,833

(22) Filed: Oct. 16, 2006

(65) Prior Publication Data

US 2008/0086918 A1    Apr. 17, 2008

(51) Int. Cl.
*A61F 5/14*     (2006.01)
*A43B 3/12*    (2006.01)
(52) U.S. Cl. .............................. 36/94; 36/11.5; D2/916
(58) Field of Classification Search ..................... 36/94, 36/95, 140, 141, 11.5, 138; D2/916, 919; D28/61
See application file for complete search history.

(56) References Cited

U.S. PATENT DOCUMENTS

| | | | | |
|---|---|---|---|---|
| 4,017,987 A | * | 4/1977 | Perez et al. ................... 36/11.5 |
| 4,207,880 A | * | 6/1980 | Zinkovich .................... 602/30 |
| D260,047 S | * | 8/1981 | Heinz .......................... D2/916 |
| D271,156 S | * | 11/1983 | Williamson .................. D2/916 |
| D400,694 S | * | 11/1998 | Kang ........................... D2/919 |
| 5,870,837 A | * | 2/1999 | Poulos ........................ 36/11.5 |
| D414,019 S | * | 9/1999 | Kang ........................... D2/916 |
| 5,946,823 A | * | 9/1999 | Yates .......................... 36/11.5 |
| D481,828 S | * | 11/2003 | Goldberg et al. ............. D28/56 |
| 2003/0145492 A1 | * | 8/2003 | Brooks .......................... 36/94 |

* cited by examiner

*Primary Examiner*—Jila M Mohandesi
(74) *Attorney, Agent, or Firm*—Alan Kamrath; Kamrath & Associates PA

(57) ABSTRACT

A portable shoe comprises a shoe body and a toe-separating massager, wherein the shoe body having a shoe sole and a vamp, and a front end of the top surface of the shoe sole is formed with a containing groove for fixing the toe-separating massager. The toe-separating massager is disposed with a plurality of separating posts and engaging grooves on the top surface thereof that are arranged staggered, and each engaging groove is engaged with a rotatable biochemical ball. By such arrangements, when the user puts on the shoe, the present invention can rectify the positions of the toes and can massage the toes by the bioelectricity discharged by the biochemical balls.

5 Claims, 5 Drawing Sheets

PORTABLE SHOE

BACKGROUND OF THE INVENTION

1. Field of the Invention

The present invention relates to a shoe, and more particularly to a portable shoe which has the function of rectifying and massaging the toes.

2. Description of the Prior Art

The so-called extroversion of the big toe means that the joint of the big toe and the first thenar bone (namely metatarsus) is outward bended for more than 15 degrees, such that an inner side of the head portion of the first metatarsus will be bulged to cause pains, and sometimes the bulged bone is swelled just like an osteoma, and even the big toe will step over the second toe. Therefore, the patient feels inconvenient and troublesome in daily life. This condition occurred in males is almost the same as that of females, in addition to the hereditary reason, it is relate to the shoes.

In order to improve the above-mentioned condition, in addition to have an operation, the patients can choose different kinds of rectifiers to rectify the extroversion of the big toe, such as a conventional toe separator 10 as shown in FIG. 1 which is made of silica gel. When using, the toe separator 10 is stuffed between the big toe and the second toe of the patient to keep the relative position of those two toes and prevent the big toe from being bended outwardly, thus rectifying the extroversion of the big toe and alleviating the pains.

Since the toe separator 10 is an independent flexible block, it is unstable, after a period of using, the upper and rear ends of the toe separator 10 will be reversely squeezed by the big toe and the second toe, so that the toe separator 10 will be deformed and unable to fix the toes.

The present invention has arisen to mitigate and/or obviate the afore-described disadvantages.

SUMMARY OF THE INVENTION

The present invention is to provide a portable shoe comprises a shoe body and a toe-separating massager, wherein the shoe body having a shoe sole and a vamp. The shoe sole is formed with a high elastic layer, and a front end of the top surface of the shoe sole is formed with a containing groove. The toe-separating massager is fixed in the containing groove of the shoe sole, and having an arc-shaped piece that is disposed with a plurality of separating posts and engaging grooves on the top surface thereof that are arranged staggered, and each engaging groove is engaged with a rotatable biochemical ball. By such arrangements, when the user puts on the shoe, the toe seams will clip the separating posts respectively, and the toes will press the biochemical balls.

The primary objective of the present invention is to provide a portable shoe, wherein the toe-separating massager is stable, and can fix the toes effectively, thus rectifying the extroversion of the big toe and alleviating the pains.

The further objective of the present invention is to provide a portable shoe, wherein the toe-separating massager is engaged with rotatable biochemical balls so as to massage the toes of the user by the bioelectricity discharged by the biochemical balls.

The present invention will become more obvious from the following description when taken in connection with the accompanying drawings, which show, for purpose of illustrations only, the preferred embodiments in accordance with the present invention.

DETAILED DESCRIPTION OF THE PREFERRED EMBODIMENTS

Figure 1:
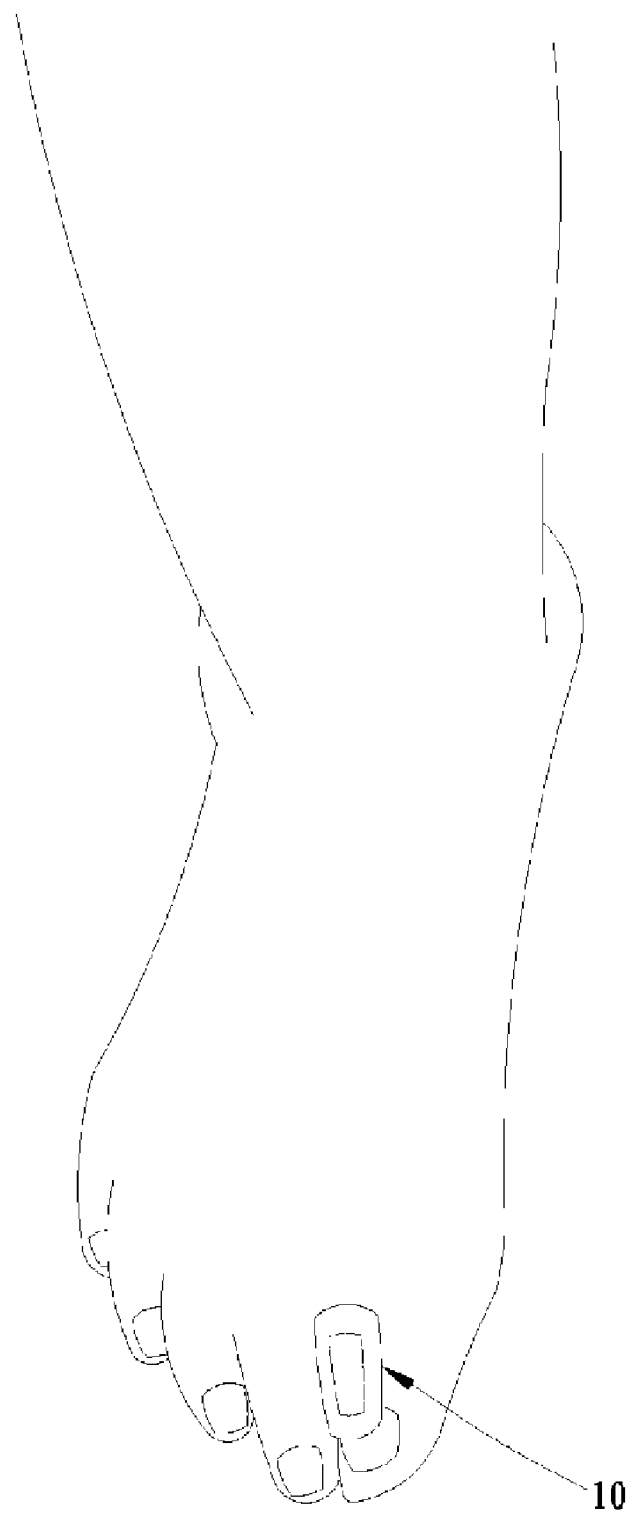
FIG. 1 is a perspective view of a conventional toe separator.
Figure 2:
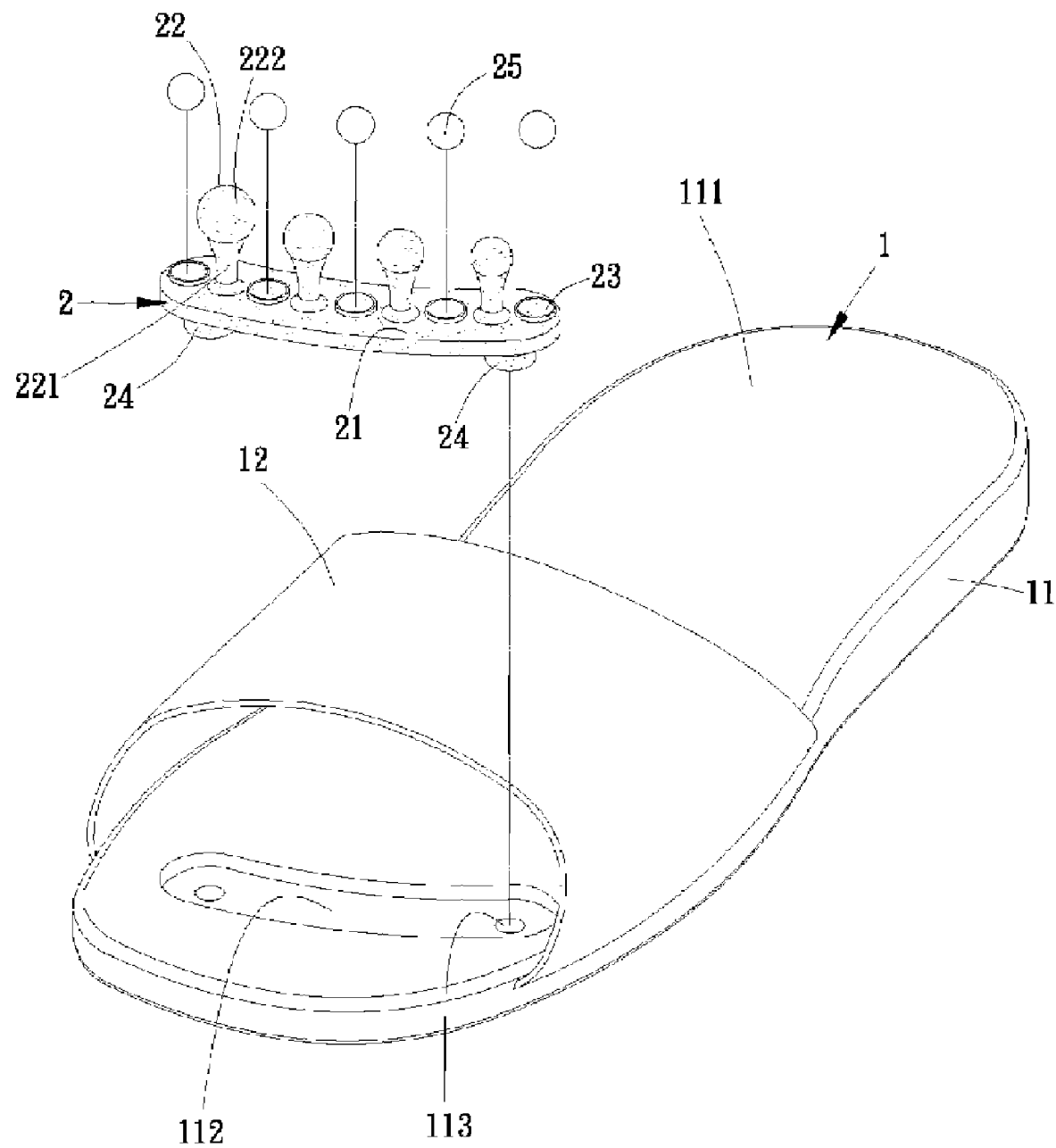
FIG. 2 is an exploded view of a portable shoe in accordance with a first embodiment of the present invention.
Figure 3:
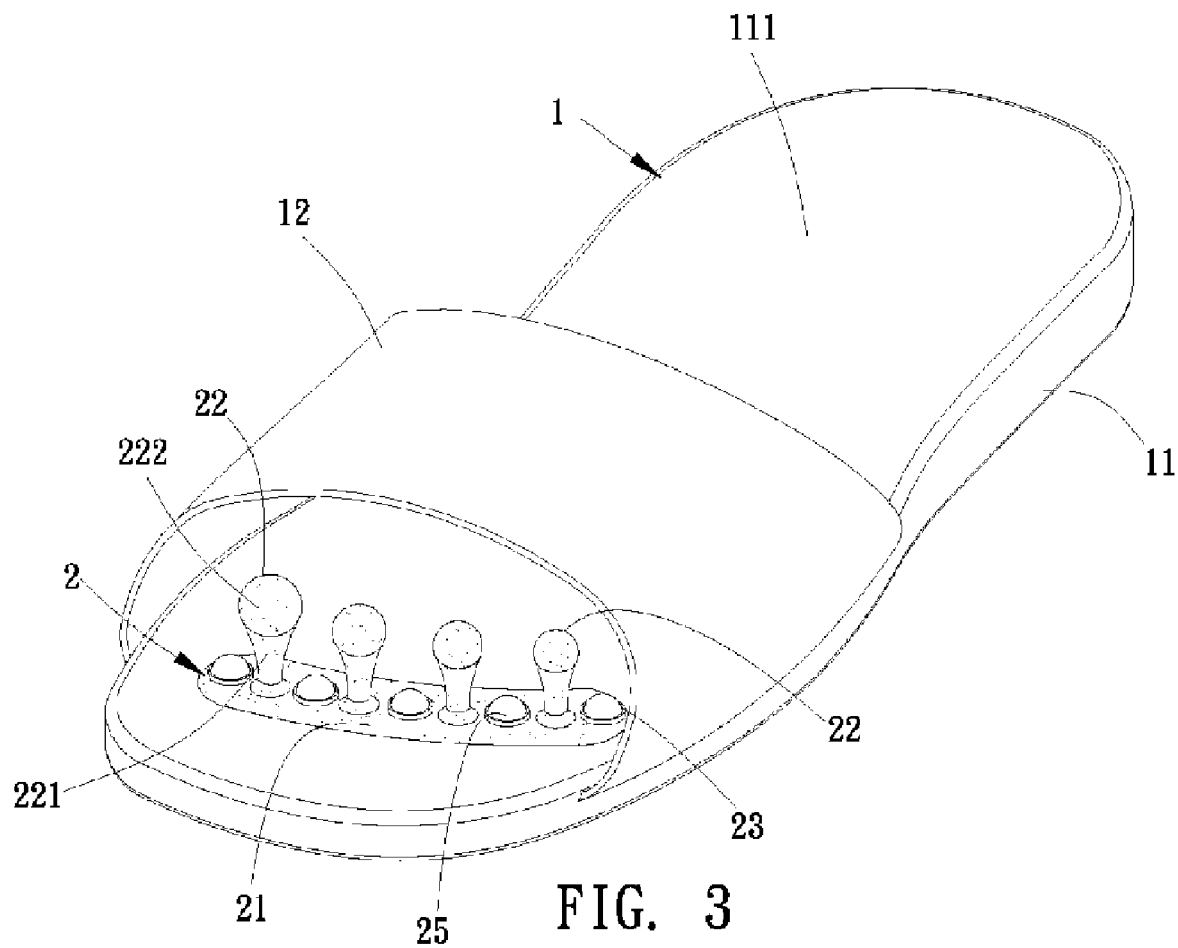
FIG. 3 is an assembly view of the portable shoe in accordance with the first embodiment of the present invention.
Figure 4:
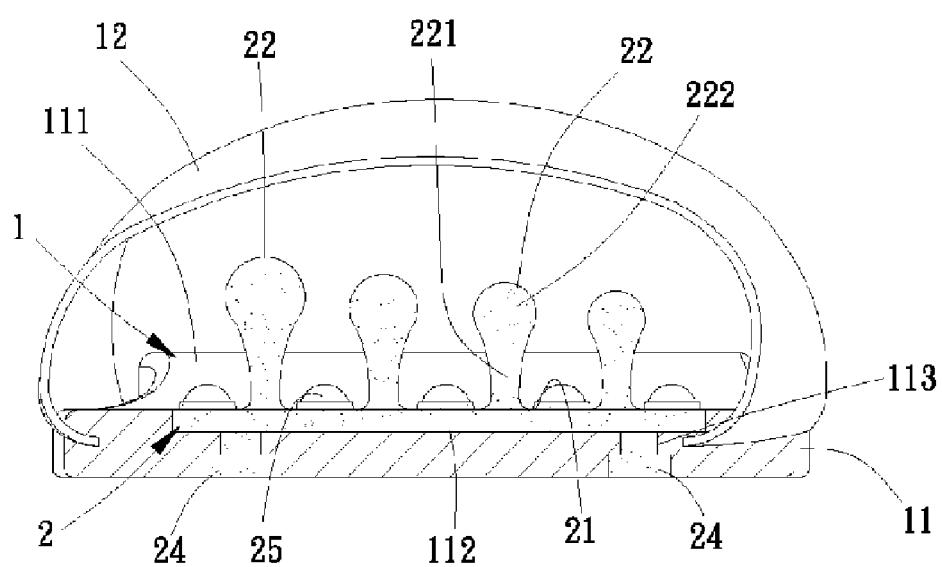
FIG. 4 is an assembly cross sectional view of the portable shoe in accordance with the first embodiment of the present invention.

Referring to FIGS. 2-4, a portable shoe in accordance with a first embodiment of the present invention comprises a shoe body 1 and a toe-separating massager 2, wherein the shoe body 1 having a shoe sole 11 and a vamp 12. The shoe sole 11 is formed with a high elastic layer 111 (such as memory soak cotton and flexible rubber), a front end of the top surface of the shoe sole 11 is formed with a containing groove 112, and both ends of the containing groove 112 is defined with a reverse T-shaped through hole 113. The shape of the vamp 12 is changeable, and the vamp 12 of the present invention is arc-shaped. The toe-separating massager 2 having an arc-shaped piece 21 that is disposed with a plurality of separating posts 22 and engaging grooves 23 on the top surface thereof that are arranged staggered, both ends of the toe-separating massager 2 are disposed with a reverse T-shaped post 24. The separating post 22 is made of flexible material, and having an awl-shaped post body 221 and a spherical head portion 222, and the sizes of the separating posts 22 are different. The engaging groove 23 is engaged with a rotatable biochemical ball 25 that is made of anion, far infrared ray and germanium.

When assembling, the toe-separating massager 2 is retained in the containing groove 112 of the shoe sole 11, and the reverse T-shaped posts 24 of the toe-separating massager 2 are passed through the reverse T-shaped through holes 113, such that the arc-shaped piece 21 of the toe-separating massager 2 is at the same level with the shoe sole 11.

Figure 5:
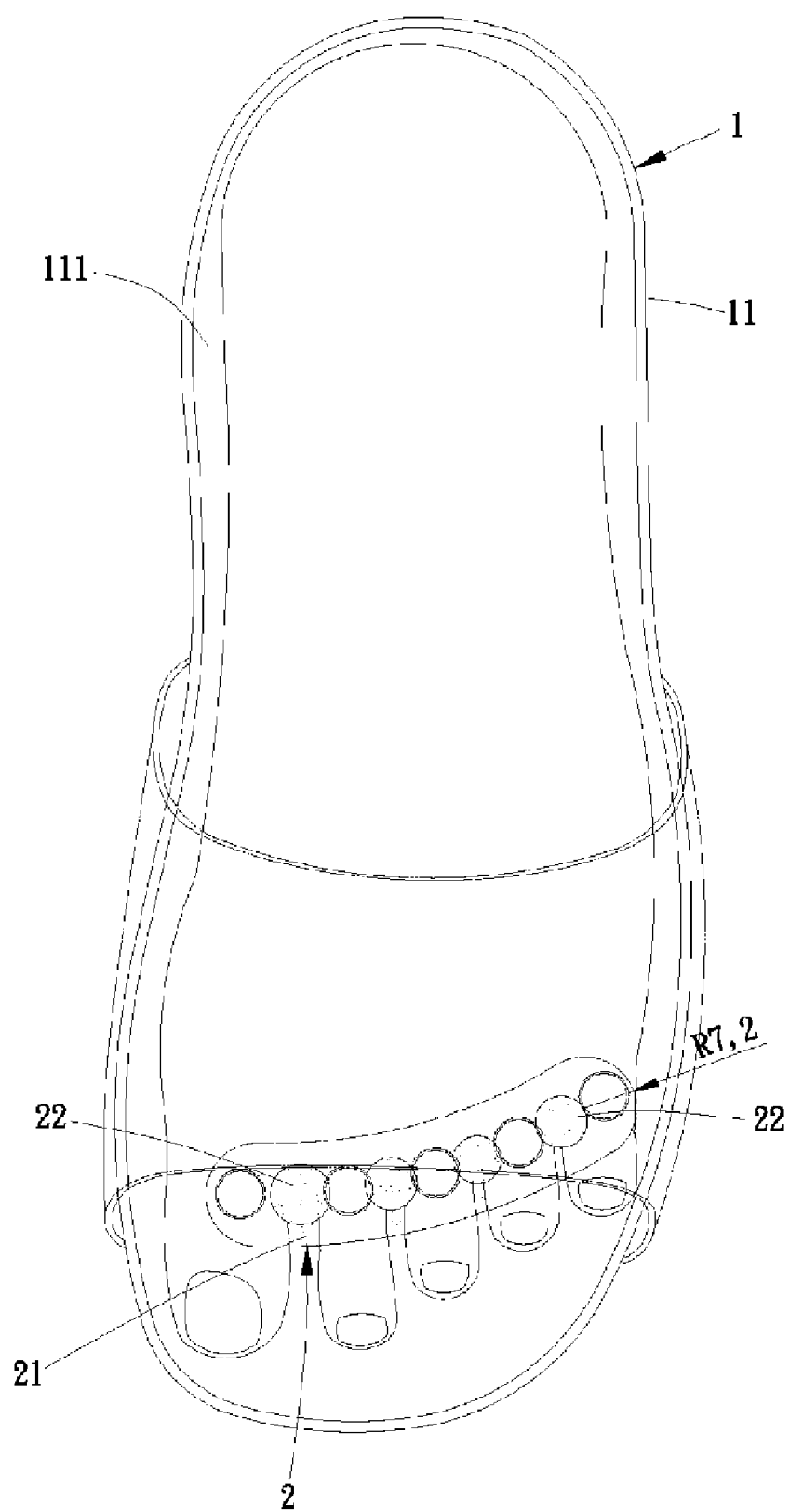
FIG. 5 is a perspective view of the portable shoe in accordance with the first embodiment of the present invention.

With reference to FIG. 5, when the user puts on the shoe, the toe seams will clip the post bodies 221 of the separating posts 22 respectively, and the respective toe 3 will press the biochemical ball 25 by the stopping of the spherical head portion 222 of the separating posts 22. By such arrangements, the toes 3 of the user can be separated and fixed to the suitable positions by the separating posts 22, thus rectifying the toes 3 and alleviating or even eliminating the partial pains caused by the abnormality of the toes 3. Furthermore, since the respective toe 3 presses the rotatable biochemical ball 25, the toes 3 can be massaged by the bioelectricity discharged by the biochemical balls 25.

Figure 6:
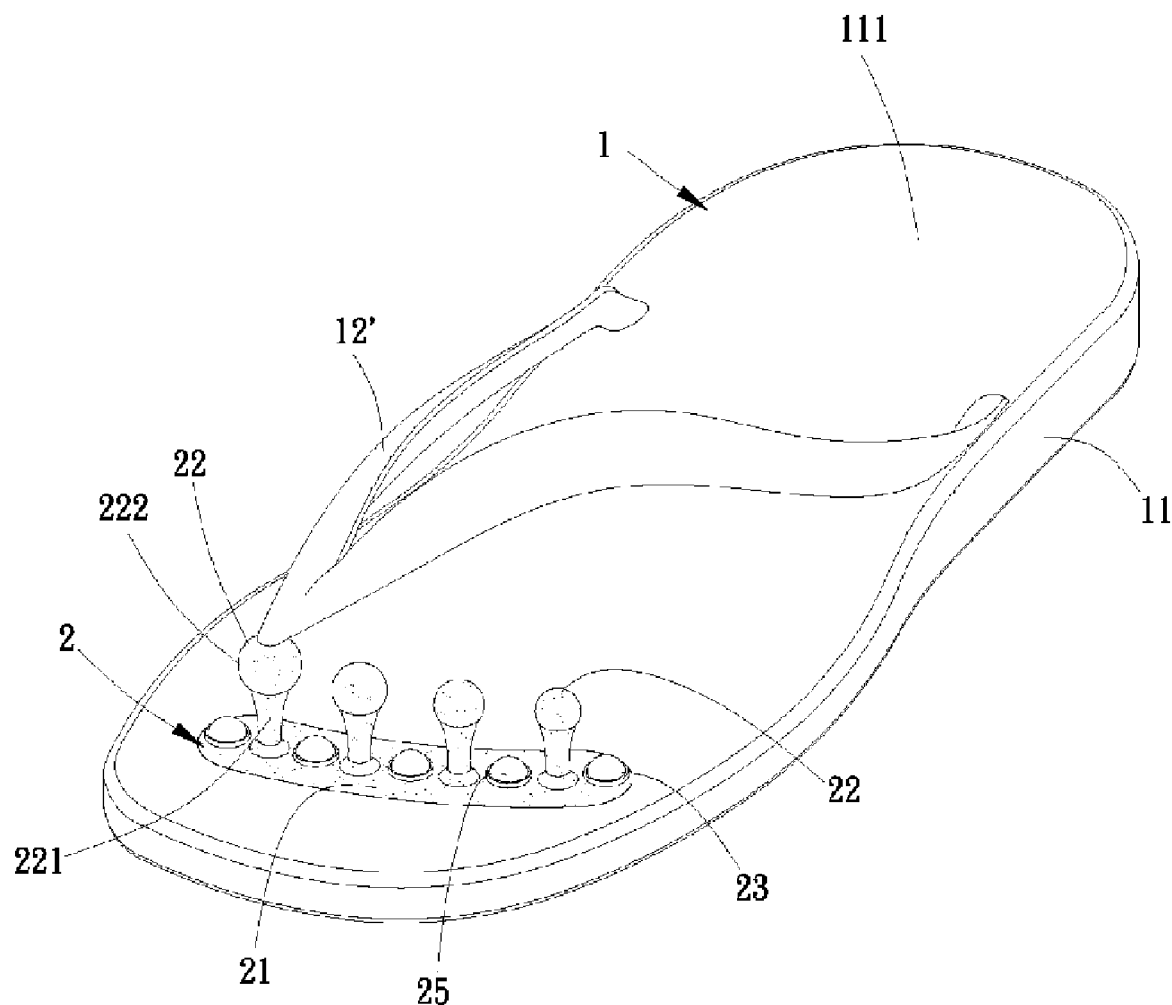
FIG. 6 is an assembly view of the portable shoe in accordance with a second embodiment of the present invention.

Referring to FIG. 6, a portable shoe in accordance with a second embodiment of the present invention is shown, wherein a vamp 12' of the shoe body 1 is integrally formed with the toe-separating massager 2, and the vamp 12' is Y-shaped. A front end of the vamp 12' is connected to the first separating post 22 of the toe-separating massager 2, and both rear ends of the vamp 12' are combined with the shoe sole 11, thus obtaining the same effects as that of the first embodiment.

By the above-mentioned structure, the present invention has the following advantages:

Firstly, the toe-separating massager 2 is fixed to the shoe body 1 directly, so that the toe-separating massager 2 is stable, when the user puts on the shoe, the toes 3 of the user can be fixed, thus rectifying the toes 3 and alleviating the partial pains caused by the abnormality of the toes 3.

Secondly, the toe-separating massager 2 is inlayed with rotatable biochemical balls 25, so the toe-separating massager 2 has the function of massaging by the bioelectricity discharged by the biochemical balls 25.

While we have shown and described various embodiments in accordance with the present invention, it should be clear to those skilled in the art that further embodiments may be made without departing from the scope of the present invention.

What is claimed is:

1. A portable shoe, comprising: a shoe body and a toe-separating massager, wherein the shoe body having a shoe sole and a vamp, which characterized in that:

the shoe body, a front end of a top surface of the shoe sole being formed with a containing groove;

the toe-separating massager being fixed in the containing groove of the shoe sole, and having an arc-shaped piece that is disposed with a plurality of separating posts and engaging grooves on the top surface thereof that are arranged staggered, the separating post being made of flexible material, and having an awl-shaped post body and a spherical head portion, the sizes of the separating posts are different, and each engaging groove being engaged with a rotatable ball.

2. The portable shoe as claimed in claim 1, wherein the shoe sole is formed with a high elastic layer.

3. The portable shoe as claimed in claim 1, wherein the toe-separating massager having an arc-shaped piece.

4. The portable shoe as claimed in claim 1, wherein the balls engaged in the engaging grooves of the toe-separating massager are biochemical balls.

5. The portable shoe as claimed in claim 1, wherein the toe-separating massager is integrally formed with the vamp, a first separating post of the toe-separating massager is connected to a front end of the vamp, and both rear ends of the vamp are combined with the shoe sole.

* * * * *